US008361095B2

(12) United States Patent  
Osborne (10) Patent No.: US 8,361,095 B2
(45) Date of Patent: Jan. 29, 2013

(54) LOOP THROMBECTOMY DEVICE

(75) Inventor: Thomas A. Osborne, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 522 days.

(21) Appl. No.: 12/372,352

(22) Filed: Feb. 17, 2009

(65) Prior Publication Data

US 2010/0211087 A1    Aug. 19, 2010

(51) Int. Cl.
A61B 17/22 (2006.01)

(52) U.S. Cl. .................................................. 606/159

(58) Field of Classification Search .............. 606/108, 606/127, 159, 200; 600/569; 604/22
See application file for complete search history.

(56) References Cited

U.S. PATENT DOCUMENTS

| 2,763,104 | A | * | 9/1956 | Lindenborg ................. 451/469 |
| 4,108,162 | A | * | 8/1978 | Chikashige et al. ......... 600/569 |
| 4,227,537 | A | * | 10/1980 | Suciu et al. ................. 600/569 |
| 4,561,439 | A | | 12/1985 | Bishop et al. |
| 5,011,488 | A | * | 4/1991 | Ginsburg ..................... 606/159 |
| 5,269,751 | A | | 12/1993 | Kaliman et al. |
| 5,370,653 | A | | 12/1994 | Cragg |
| 5,376,100 | A | | 12/1994 | Lefebvre |
| 5,851,171 | A | * | 12/1998 | Gasson .......................... 600/3 |
| 5,968,057 | A | | 10/1999 | Taheri |
| 5,984,965 | A | | 11/1999 | Knapp et al. |
| 6,156,062 | A | | 12/2000 | McGuinness |
| 6,338,739 | B1 | | 1/2002 | Datta et al. |
| 6,397,855 | B1 | * | 6/2002 | Dumler ......................... 132/218 |
| 6,454,775 | B1 | | 9/2002 | Demarais et al. |
| 6,530,935 | B2 | | 3/2003 | Wensel et al. |
| 6,652,548 | B2 | | 11/2003 | Evans et al. |
| 6,685,722 | B1 | | 2/2004 | Rosenbluth et al. |
| 6,692,509 | B2 | | 2/2004 | Wensel et al. |
| 6,866,680 | B2 | | 3/2005 | Yassour et al. |
| 6,926,725 | B2 | | 8/2005 | Cooke et al. |
| 6,929,709 | B2 | | 8/2005 | Smith |
| 6,974,473 | B2 | | 12/2005 | Barclay et al. |
| 6,986,784 | B1 | | 1/2006 | Weiser et al. |
| 7,037,316 | B2 | | 5/2006 | McGuckin, Jr. et al. |
| 2005/0177246 | A1 | | 8/2005 | Datta et al. |
| 2005/0228417 | A1 | * | 10/2005 | Teitelbaum et al. .......... 606/159 |
| 2006/0184194 | A1 | * | 8/2006 | Pal et al. ........................ 606/200 |
| 2007/0191866 | A1 | * | 8/2007 | Palmer et al. ................. 606/127 |
| 2007/0198028 | A1 | * | 8/2007 | Miloslavski et al. ......... 606/127 |

\* cited by examiner

Primary Examiner — Ryan Severson
Assistant Examiner — David Eastwood
(74) Attorney, Agent, or Firm — Brinks Hofer Gilson & Lione (57) ABSTRACT

A thrombectomy device may include an elongate torsion member having a proximal end and a distal end, and a plurality of helically arranged engagement members disposed at a distal portion of the elongate torsion member. Preferably, at least a portion of the engagement members has a rounded, atraumatic shape. The engagement members have a collapsed state where the engagement members are compressed toward the elongate torsion member, and an expanded state where the engagement members are expanded radially outward. Preferably, the engagement members are attached to and extends radially outward from the elongate torsion member at a different longitudinal point such that the engagement members are spaced longitudinally and circumferentially from each other when in the expanded state. When the thrombectomy device is deployed in a body lumen or cavity, the engagement members expands out to contact a wall of the body lumen or cavity.

17 Claims, 9 Drawing Sheets

LOOP THROMBECTOMY DEVICE

BACKGROUND

This invention relates generally to medical devices and particularly to a device for removing blood clots, or thrombi, from body vessels, such as the small arteries associated with the brain.

The presence of blood clots or thrombus in the vascular system is a very dangerous condition that if left untreated can cause serious and potentially life-threatening disease. Thrombi within the vasculature can form as a result from a variety of causes, such as trauma, disease, surgery, stagnant flow of blood, and foreign devices in the vasculature. Typically, a thrombus present in an arterial blood vessel tends to migrate in the direction of flow from a large diameter artery to smaller diameter arteries. The thrombus continues to flow with the blood until it becomes lodged against the vessel wall and is unable to advance. In some instances, the thrombus partially or completely blocks blood flow through the artery thereby preventing blood from reaching the tissue disposed downstream of the thrombus. Denying blood flow for an extended period of time can result in damage or death of the tissue beyond this point. The result can be loss of toes or fingers, or even entire legs in more severe circumstances. Moreover, thrombi in the venous system can migrate to the lungs and become a pulmonary embolus, which is usually fatal. In other instances, thrombi can migrate into the cerebral circulation and cause stroke and death.

Currently, thrombus removal, or thrombectomy, may be performed in a variety of ways. For example, the clot may be dissolved through chemical lysis using drugs. While this method is adequate, clot lysis has significant disadvantages in that it is a very slow process taking hours or even days to complete. Additionally, the drugs utilized in clot lysis cause the blood to thin, thereby leaving a patient susceptible to serious hemorrhage complications.

Thrombectomy may also be performed using mechanical devices. Typically, these devices are inserted into a patient's vasculature and delivered to a treatment site over a guide wire using the Seldinger or modified Seldinger technique, which is well known in the art. Generally, these mechanical devices have the disadvantage that they are usually not strong enough or dense enough to adequately capture and remove a thrombus. This is because these devices must be small and flexible in order to negotiate the tortuous anatomy where clots are likely to be found.

One type of common thrombectomy device is a balloon that is inflated in a vessel and then withdrawn to pull a clot(s) into a conventional sheath. The sheath may then be withdrawn from the patient to remove the captured clot(s). Other devices are simple open ended catheters into which a clot is aspirated and removed from the patient.

Although adequate for some applications, these devices have disadvantages. For example, the balloon catheter devices must be first advanced through the clot before they can be inflated and retracted. The process of penetrating the clot with the balloon catheter device tends to push the clot deeper into the arterial circulation where it becomes even more difficult to remove. Further, this system is not well suited to small vessels (below about 3.5 mm) because the catheter portion begins to approach the size of the vessel being treated, making it even more difficult, if not impossible to penetrate the thrombus without pushing it further into the vessel. Additionally, these mechanical devices must be designed so that they do not damage the vessel wall during the thrombectomy process, which may result in further clotting. As a result, the structure of these devices is typically very flimsy, thus compromising the ability to actually retain the clot during the removal process.

These same issues also plague devices using wire spirals or coils that can be collapsed and expanded into the clot, or basket like devices that are expanded inside of or distal to the thrombus and then retracted in an effort to pull the thrombus out of the vessel. These devices frequently collapse during the withdrawal process or actually macerate the thrombus into finer clots which then can migrate farther downstream, making them even harder to capture.

Still other devices utilize corkscrew shaped members that are collapsed into an outer delivery sheath and passed through the clot before they can be deployed and retracted. The action of pushing a device through the center of the clot forces the clot deeper into the artery and may fragment the clot, making it an even more dangerous embolus. Typically, such corkscrew devices have a smooth rounded tip to prevent the corkscrew from penetrating the vessel wall or otherwise damaging the vessel wall as it is screwed into the clot. With these devices, however, the smooth, rounded central tip itself does not screw into the clot; rather the central tip is pushed into the clot and then the remainder of the corkscrew is screwed into the clot. As with basket, coil, and balloon devices, this pushing force may also force the thrombus deeper into the vessel. Further, the corkscrew also exerts a pulling force on the periphery of the clot in addition to the pushing force focused on the center of the clot. These counter forces tend to macerate or fragment the clot and result in only a small part of the clot being captured. Some corkscrew devices may substitute a sharp tip that can screw directly into the clot. However, sharp tips can penetrate the vessel wall just as easily as they can penetrate and capture the clot. Accordingly, such devices are seldom used since they carry the very high risk of penetrating the vessel wall. Further, when a bead or ball is applied to the tip of the device that is large enough to protect the vessel wall, it is usually so large that it will tend to push the clot distally rather than penetrate the clot such that the clot can be captured and removed.

Another disadvantage common to conventional balloon, coil, basket, and corkscrew thrombectomy devices is that they tend to have relatively large cross-sectional profiles and, in turn, are overly stiff for use in small tortuous vessels of the brain. Therefore, it has become apparent to the inventor that a need exists for an improved mechanical thrombectomy device.

SUMMARY

Thrombectomy devices are described which may allow for a lower profile configuration that adaptably expands to contact a vessel wall and minimizes or eliminates maceration of a thrombus. The invention may include any of the following aspects in various combinations and may also include any other aspect described below in the written description or in the attached drawings.

In one embodiment a thrombectomy device may include an elongate torsion member having a proximal end and a distal end, and a plurality of helically arranged engagement members disposed at a distal portion of the elongate torsion member. Preferably, at least a portion of the engagement members has a rounded, atraumatic shape. The engagement members have a collapsed state where the engagement members are compressed toward the elongate torsion member, and an expanded state where the engagement members are expanded radially outward. Preferably, the engagement members are attached to and extend radially outward from the elongate torsion member at different longitudinal points such that the engagement members are spaced longitudinally and circumferentially from each other when in the expanded state.

In one aspect, when the thrombectomy device is deployed in a body lumen or cavity, the engagement members expands out such that the rounded atraumatic shaped portion of the engagement members are in contact with a wall of the body lumen or cavity. In one embodiment, an entirety of the engagement members consists of a loop of wire having a rounded atraumatic shape that extends from the longitudinal point on the torsion member in a continuous manner. Preferably, the wire is made of a material having super-elastic characteristics.

In some embodiments, the elongate torsion member may be a metallic shaft made from a flexible metallic material and the wire of each of the engagement members is permanently attached to the different longitudinal points. In other embodiments, the elongate torsion member is a torque cable that is woven from a plurality of metallic wire strands. In this embodiment, the wire forming the engagement members may be a single continuous wire woven into the torque cable, or each engagement member may be made of a separate wire. Preferably, both the strands forming the torque cable and the wire forming the engagement members are made of nitinol.

In one aspect, a torque shaft may be fixedly attached to the proximal end of the elongate torsion member. In another aspect, a handle may engage the torque shaft such that when the handle is rotated, the engagement members are also rotated.

In one embodiment, the thrombectomy device may also include an inner sheath disposed around the elongate torsion member. Preferably, the inner sheath has a diameter that is less than an outer diameter of the helical arrangement of engagement members in the expanded state, and includes a spring member disposed at a distal end thereof. The spring member preferably has a compressed configuration in which a diameter of the spring member is substantially equal to a diameter of the inner sheath, and an expanded configuration in which at least a portion of the spring member has a diameter that is larger than the diameter of the inner sheath. In one aspect, the spring member may have a proximal end that is restrained and a distal end that is unrestrained in the expanded state, such that the spring member has a cone like shape when expanded.

In another aspect, a substantially inelastic outer sheath may be disposed on an outer surface of the inner sheath and slidably movable thereupon, the outer sheath thereby restraining the spring member in the compressed configuration.

A method of using a thrombectomy device may include introducing the thrombectomy device percutaneously into a body lumen or cavity proximal of a thrombosis and expanding the device such that the plurality of engagement members are in the expanded state and at least a portion thereof contacts a wall of said body lumen or cavity.

The device is rotatably advanced toward the thrombus such that the rounded atraumatic shape of the engagement members translate longitudinally along the wall of the lumen or cavity in a corkscrew shaped path. As the thrombectomy device is rotatably advanced, the thrombus is twistingly engaged by the plurality of helically arranged engagement members such that the thrombus is captured within the helical arrangement of engagement members.

In one aspect, if the thrombectomy device includes an inner sheath disposed around the elongate torsion member, the inner sheath comprising a compressed spring member disposed at a distal end thereof, the spring member may be expanded, thereby causing the distal end of the inner sheath to expand radially. The thrombectomy device including the captured thrombus is then retracted into the inner sheath through the expanded distal end. In another aspect, the thrombectomy device is linearly withdrawn into the inner sheath. In yet another aspect the thrombectomy device is rotatably withdrawn into the inner sheath.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION

Figure 1:
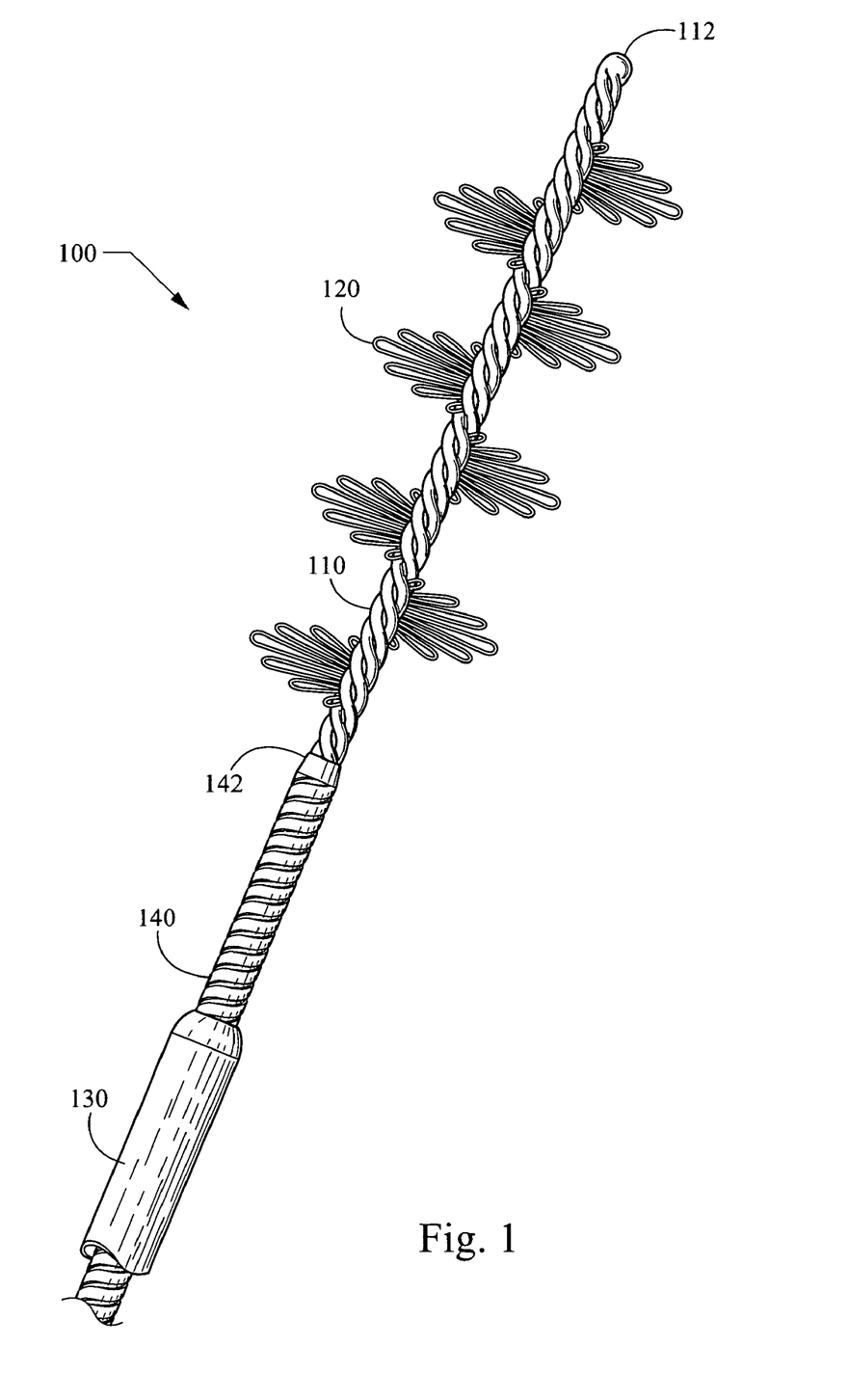
FIG. 1 is a side elevation view of a distal end of a thrombectomy device in an expanded configuration.
Figure 2:
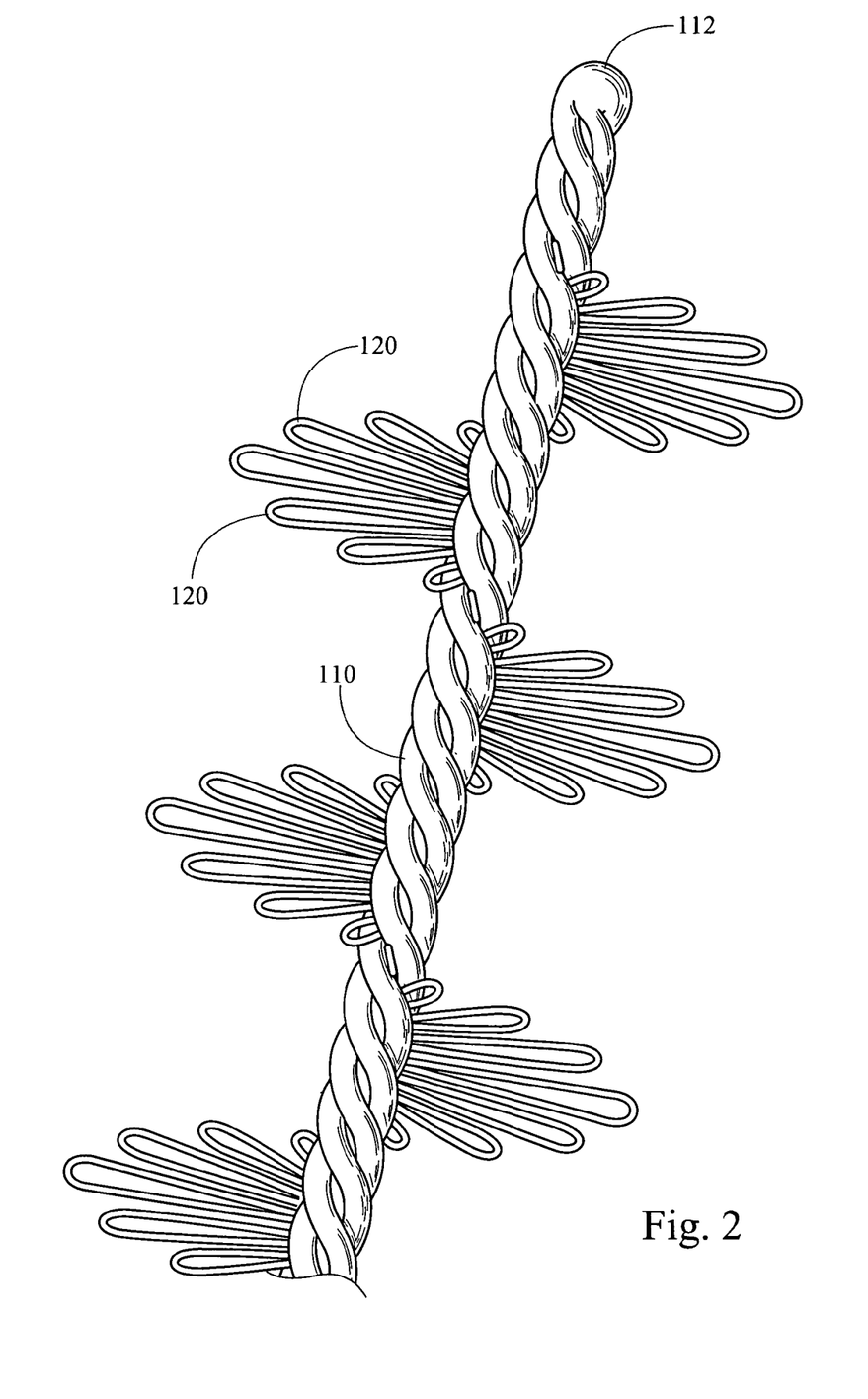
FIG. 2 is a close-up view of the distal end of the thrombectomy device of FIG. 1.

Referring now to the Figures, FIGS. 1 and 2 illustrate a distal portion of a thrombectomy device 100 according to an embodiment of the present invention. The thrombectomy device preferably includes an elongate torsion member 110 and a plurality of engagement members 120. The plurality of helically arranged engagement members 120 are disposed at a distal portion of the elongate torsion member 110, each engagement member having a collapsed state, in which the engagement members 120 are compressed radially inward toward the elongate torsion member 110, and an expanded state, in which the engagement members 120 are expanded radially outward away from the elongate torsion member 110. Preferably, the engagement members 120 extend perpendicularly away from the surface of the elongate torsion member 110. Other angles of extension are contemplated, including angles toward and away from a distal end of the elongate torsion member 110.

In one embodiment the torsion member 110 is formed from a flexible shaft or cable. In one embodiment, the elongate torsion member 110 is a hollow shaft that is configured to receive and be passed over a guide wire. In another embodiment, the elongate torsion member 110 may be a solid metallic, polymer, or composite shaft. Regardless of the construction, the elongate torsion member 110 preferably includes a blunt atraumatic tip 112 disposed at its distal-most end to prevent the thrombectomy device 100 from accidentally damaging tissue or puncturing a vessel or cavity wall during use.

Preferably the elongate torsion member 110 is torsion cable that consists of a plurality of braided wire strands. The braided configuration of the torsion cable provides flexibility in the radial direction, but minimizes spring-like energy storage from twisting and torque when rotated about its central axis. The elongate torsion member 110 is substantially incompressible in the longitudinal direction. Preferably, the elongate torsion member is formed of metallic wire strands, for example and without limitation, Nitinol or stainless steel. Other materials are contemplated as known in the art. Preferably, the elongate torsion member 110 is not a coiled (non-braided) cable as such cables tend to coil more tightly or uncoil, depending on the direction of rotation of the cable, and are not efficient at transmitting rotational force.

Figure 3:
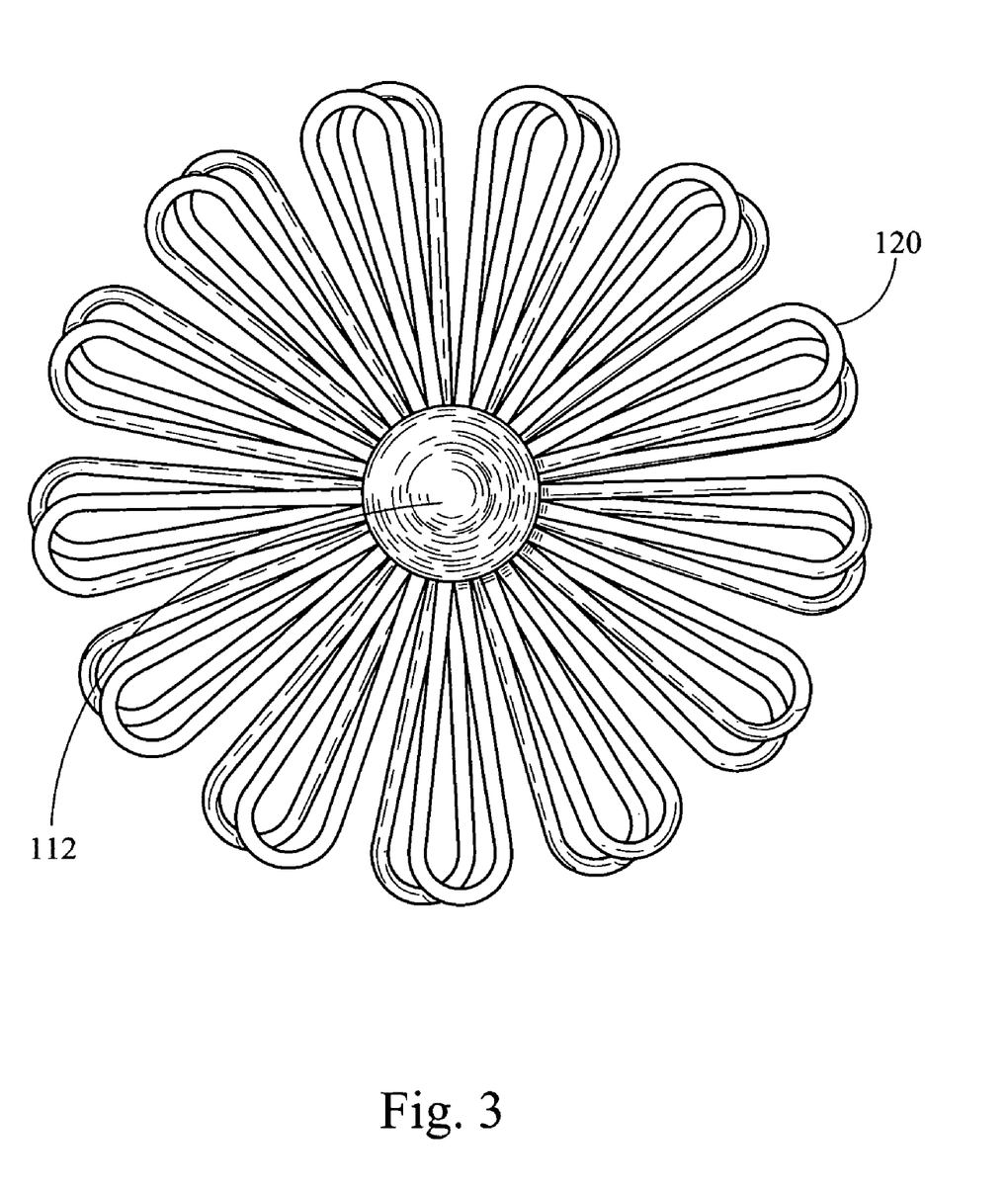
FIG. 3 is an elevation end view of the distal end of the thrombectomy device of FIG. 1.

Each of the plurality of engagement members 120 may be fixedly attached to the elongate torsion member 110 and extend outward in a radial direction. As shown in FIGS. 1 and 3, each of the engagement members 120 are disposed at longitudinal and circumferential positions and are longitudinally spaced from one another such that they form a helical arrangement around and along the elongate torsion member 110. Preferably, each engagement member 120 has the same narrow loop structure that is narrowest at the connection point on the elongate torsion member 110 and that progressively widens as the engagement member 120 moves radially outward. The radially outward most portion of each engagement member 120 preferably has a smooth, radial transition surface that arcs between the two sides of the loop, thereby providing an atraumatic surface for contacting a wall of a body lumen (e.g. blood vessel, etc.) or cavity. However, it should be understood that the engagement members are not limited thereto, and other atraumatic loop shapes are contemplated, for example and without limitation, teardrop, oval, and circular shapes.

In a preferred embodiment, the engagement members 120 are formed from a continuous length of Nitinol wire, formed as a series of "S-shaped" curved loops. The Nitinol wire may range in size from about 0.002 inches up to 0.015 inches, depending on the desired size and strength of the device. The Nitinol wire is preferably in the pseudoelastic state at body temperature to allow it to be springy and move between the compressed state, where the engagement members are folded or bent down along the elongate torsion member 110 for insertion into a delivery system or the like, and the expanded state. The wire size may be specified such that the thrombectomy device 100 is flexible and small enough for use in vessels as small as about 1 mm (e.g. cerebral vessels) or large and stiff enough for use in vessels up to about 40 mm (e.g. aorta, vena cava).

The Nitinol wire is preferably wound or otherwise incorporated into the braid structure of the elongate torsion member 110, such that the engagement members 120 are sandwiched between two windings of wire strands of the braid structure. Because the loops of the engagement members 120 extend radially outward from between the wire strands, the engagement members 120 are arranged in an angled, spiral, helical pattern, as shown in FIG. 1. Preferably, each engagement member 120 does not contact the helically adjacent engagement member(s), such that the engagement members 120 are wholly supported by the elongate torsion member 120 and are circumferentially and longitudinally spaced apart from one another to create a spiral staircase-like pathway that captures and guides a thrombus around the elongate torsion member 110. However, it should be understood that the embodiment is not limited thereto, and that helically adjacent engagement members 120 may contact or overlap with each other. Moreover, it should be understood that while Nitinol wire is utilized in the preferred embodiment, it is not limited thereto, and the wire may be made of any suitable material having elastic properties as is known in the art. Additionally, the wire may be made of a shape memory material and have a predetermined shape, e.g. curved or looped, when in an expanded state, as is known in the art. However, it should be understood that the embodiment is not limited thereto, and the wire may be made from any material that will result in a self-expanding device and may have any shape that results in a rounded, atraumatic surface for engaging a vessel wall. For example, the device may be comprised of pre-configured polymeric material, stainless steel wire, cobalt-chromium-nickel-molybdenum-iron alloy, or cobalt-chrome alloy.

In an alternative embodiment, the wire may be doped with platinum, or other radiopaque elements to increase the radiopacity of the engagement members 120 and facilitate visualization and placement using fluoroscopy.

Preferably, a torque shaft 140 is attached at a proximal end of the elongate torsion member 110 through a joint 142, by welding, soldering, adhesive bonding, or the like. An inner catheter 130 may then be formed about the torque shaft 140.

Figure 4:
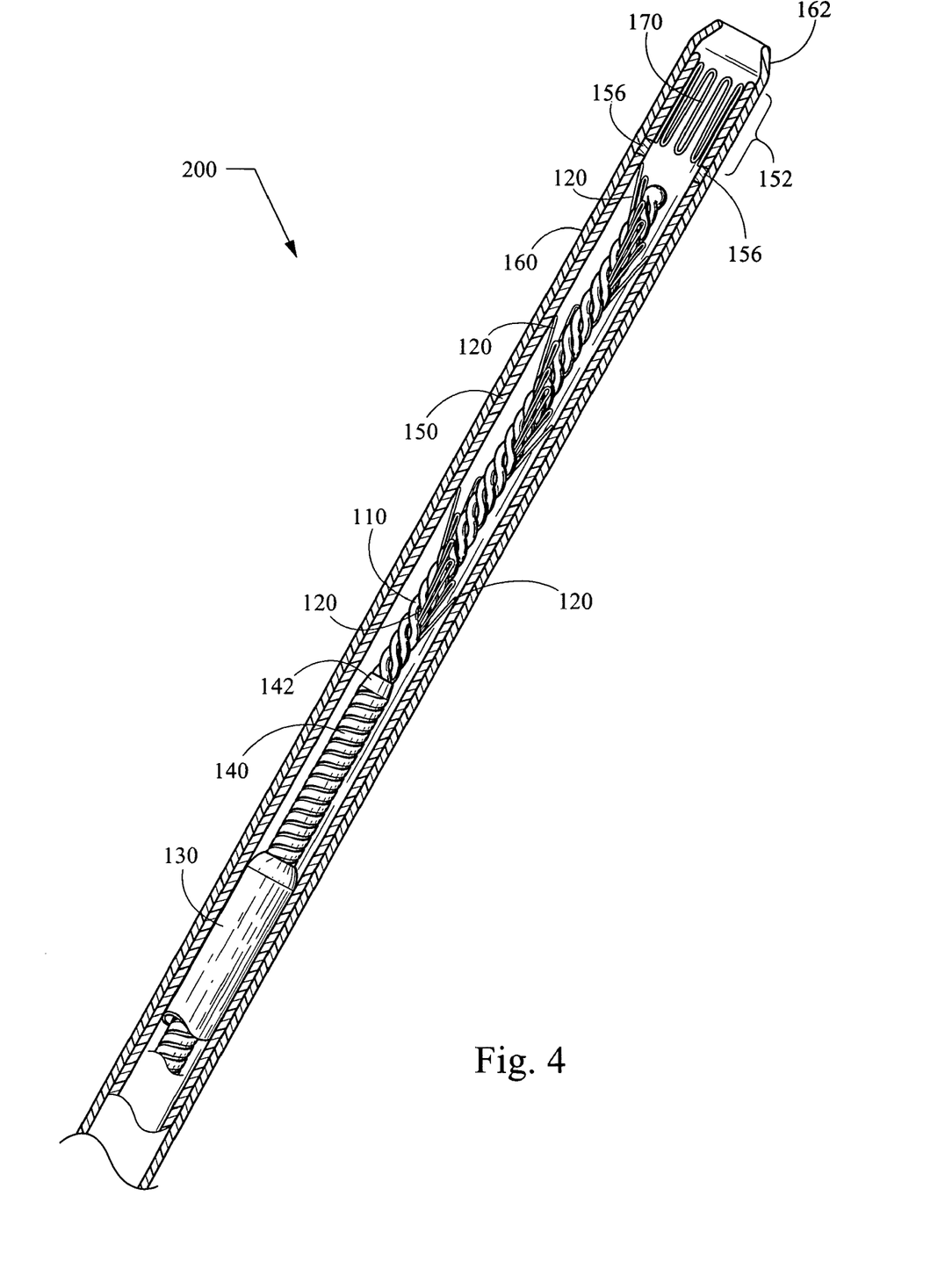
FIG. 4 is a partial cross-sectional view of the distal end of the thrombectomy device of FIG. 1 in a restrained configuration.
Figures 5A, 5B, 5C:
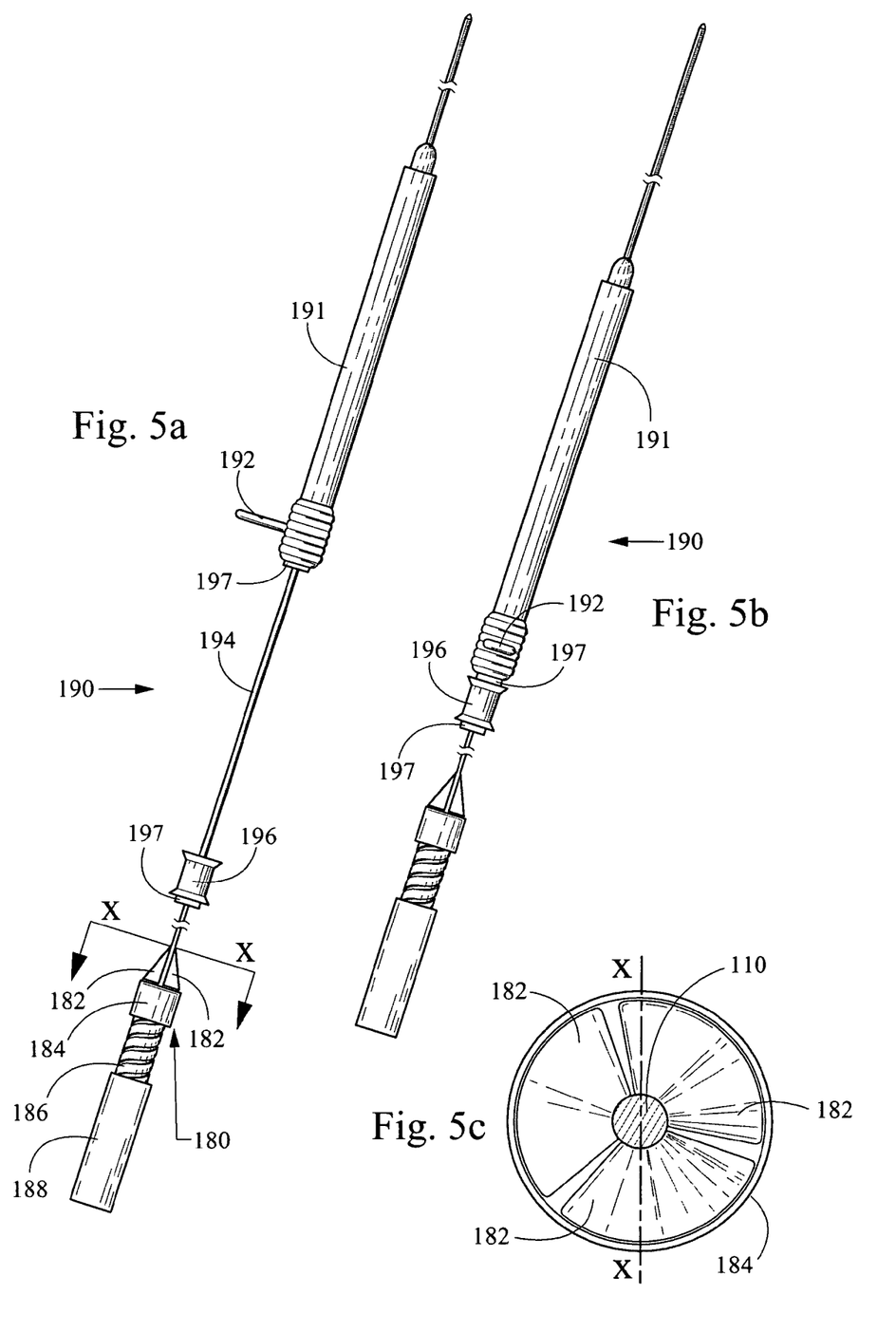
FIG. 5a is a side elevation view of a delivery system for the thrombectomy device of FIG. 4 with an outer retention sheath in an initial position.
FIG. 5b is a side elevation view of the delivery system of FIG. 5a with the outer retention sheath in a retracted position.
FIG. 5c is a cross-sectional view of a torque handle taken along the line X-X of FIG. 5b.

The thrombectomy device 100 described above may be used independently without any other delivery system or mechanism. Alternatively, the thrombectomy device 100 may be implemented using a delivery system, for example, as illustrated in FIGS. 4-5c. As shown in FIG. 4, the delivery system 200 includes an inner sheath 150 disposed about the thrombectomy device 100. Preferably, the inner diameter of the inner sheath 150 approximates, or is slightly larger than an outer diameter of the inner catheter 130 such that when the thrombectomy device 100 is inserted into the inner sheath 150, the engagement members 120 are flexed, or folded down along the elongate torsion member 110 in the compressed state. The inner sheath 150 may be made of Nylon, Teflon, or other suitable material as known in the art, and may include wire coils or braids to increase stiffness and prevent the compressed engagement members 120 from expanding or stretching the inner sheath 150 and to improve pushability and torquability of the delivery system 200 during insertion.

The inner sheath 150 includes an expandable distal portion 152 that is attached through a joint 156. A spring member 170 is housed within the expandable distal portion 152, and is held in a compressed state by an outer retention sheath 160. The outer retention sheath 160 may be made of Nylon, Teflon, Polyethylene (PTFE), or other suitable materials as known in the art. Like the inner sheath 150, the outer retention sheath 160 may also include wire braids or coils embedded in a wall thereof to facilitate control of the device. Additionally, the outer retention sheath 160 may have a tapered atraumatic distal end 162 to facilitate advancement through a patient's vasculature and prevent damage thereto. The spring member 170 may be made of super elastic or shape memory material, for example and without limitation, Nitinol.

In a preferred embodiment, the spring member 170 is a self-expanding stent made of a super elastic material, such as Nitinol, stainless steel or the like and may be formed from a single nitinol wire that is bent in a "Z-shaped" manner. Alternatively, the spring member 170 may be formed by soldering individual wires together or cut from cannula to achieve the undulating structure. The diameter of the wire or thickness of the cannula of the spring member 170 may range from about 0.002 inches to about 0.020 inches, depending on the intended use (larger diameter vessels require thicker wire to achieve the necessary expansion force). The spring member is preferably formed from undulating or "Z-shaped" stent struts that are configured to flex between a compressed configuration, in which circumferentially adjacent stent struts abut or are disposed adjacent to one another, and an expanded configuration, in which circumferentially adjacent stent struts are angled away from each other, as known in the art. More preferably, a proximal end of the spring member 170 is restrained, such that when the spring member 170 is released from the compressed configuration, the proximal ends of the stent struts are held in place, thereby leaving only the distal ends able to expand. The resulting expanded form is essentially a funnel or cone like shape that provides a smooth transition from the expanded large diameter at the distal end of the expandable distal portion 152 to the smaller original diameter approximating the inner diameter of the inner sheath 150 at the joint 156. The proximal end of the spring member 170 may be restrained by integrally forming a non-expanding continuous ring having a diameter substantially equal to the compressed configuration, or by mechanically connecting the proximal ends of the stent struts directly together or to a ring by welding, soldering, adhesive, sutures, etc., as known in the art. Preferably, the distal end of the expandable distal portion 152 is expanded such that it contacts at least a portion of the vessel/cavity wall when the spring member 170 is released from the compressed configuration.

Figure 4A:
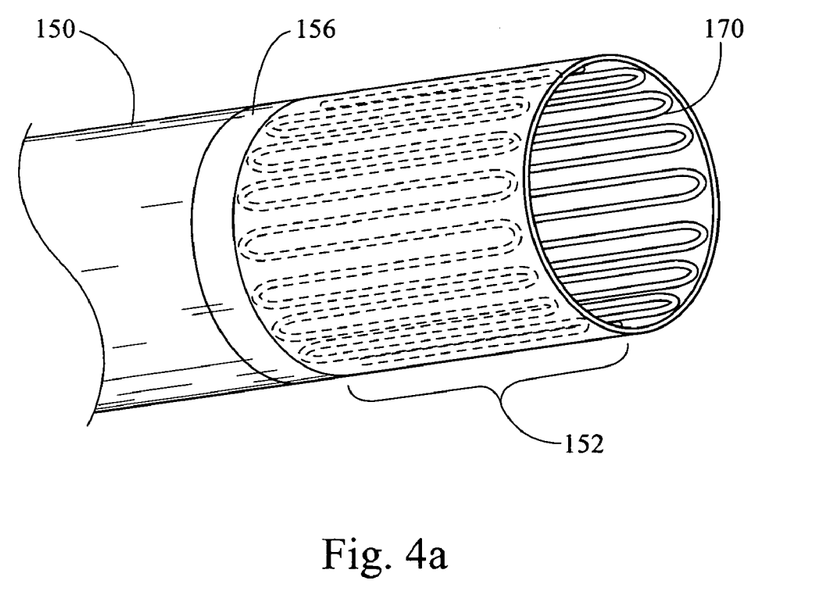
FIGS. 4a and 4b are orthogonal views of two embodiments of an expandable distal portion of an inner sheath of the thrombectomy device of FIG. 4.
Figure 4B:
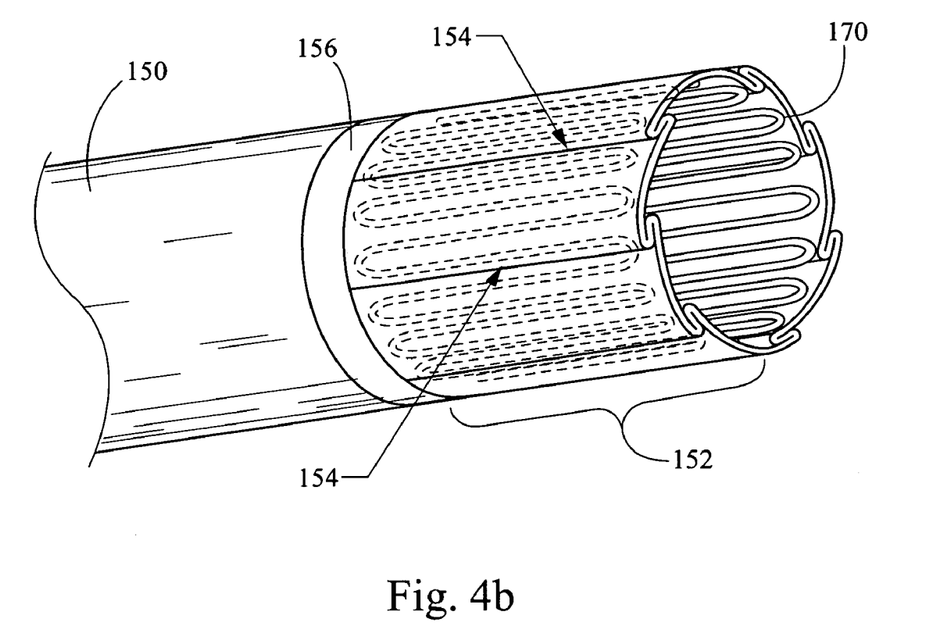

As shown in FIGS. 4a and 4b, the expandable distal portion 152 of the inner sheath 150 extends from the distal end of the inner sheath 150 proximally by an amount that substantially corresponds to the length of the spring member 170. The inner sheath 150 and the expandable distal portion 152 may be attached at the joint 156 by adhesive or thermal bonding, as known in the art. In the embodiment shown in FIG. 4a, the expandable distal portion 152 is formed from a flexible and elastic material that is radially expandable when subjected to the expansive force of the spring member 170 and collapses freely when retracted into the outer retention sheath 160. Preferably, the expandable distal portion 152 is an elastomeric material, such as ePTFE (elastic polytetrafluoroethylene), Thoralon, polyurethane, silicone rubber, or a membrane of thin polymers. Preferably, the expandable distal portion 152 has a thickness of less than one thousandth of an inch to about three thousandths of an inch. In an alternative embodiment the entire inner sheath 150 is formed of the same flexible, elastic material, thereby obviating the need for the joint 156.

FIG. 4b illustrates yet another alternative embodiment, in which the expandable distal portion 152 is made from a substantially inelastic material that is sized and shaped to conform to the desired expanded shape of the spring member 170. When the spring member 170 is in its compressed configuration under the outer retention sheath 160, portions 154 of the inelastic material are folded radially around the spring member 170 in a pleat like manner. When the outer retention sheath 160 is withdrawn in the proximal direction, it releases the spring member 170, and the inner folded portions 154 unfold, thereby allowing the spring member 170 to assume its fully expanded shape.

As shown in FIGS. 5a-c, the proximal end of the delivery system includes a control handle 190 having a handle 191, a locking pin 192 to prevent accidental or premature deployment, luer lock ports 197 for delivering radiopaque dye or clot dissolving drugs to a thrombus through the delivery system to, or removing fluid from a treatment site in a patient, a shaft 194, and a knob 196. Note that while the delivery and use of clot dissolving drugs are contemplated, the present invention may not require such drugs to eliminate thrombi. A proximal end of the outer retention sheath 160 is fixedly attached to the handle 191. In operation a physician holds the knob 196 stationary in one hand, and pulls the handle 191 in a rearward direction to retract the outer sheath 160. However, it should be understood that the embodiment is not limited thereto, and the proximal end of the delivery system 200 may utilize any sheath retracting means known in the art.

The torque shaft 140 preferably passes through a lumen in the handle 191, the shaft 194 and the knob 196. The torque shaft 140 also extends out of the proximal end of the knob 156 a sufficient amount to be engaged by a torque handle in the form of a pin vise 180. The pin vise 180 includes a handle 188, a threaded portion 186, a locking collar 184 disposed around and threadably engaging the threaded portion 186, and jaws 182. Preferably, both the lock collar 184 and the handle 188 are knurled, or otherwise textured to facilitate rotation.

In operation, the proximal end of the torque shaft 140 is inserted into a central space between the jaws 182. The lock collar is then rotated in a distally advancing direction, which forces the jaws 182 together in a radially inward direction, thereby frictionally locking the torque shaft 140 in place (see FIG. 5c). Preferably, the proximal ends of the inner and outer sheaths 150, 160 terminate in luer lock type fittings 197.

Figure 6:
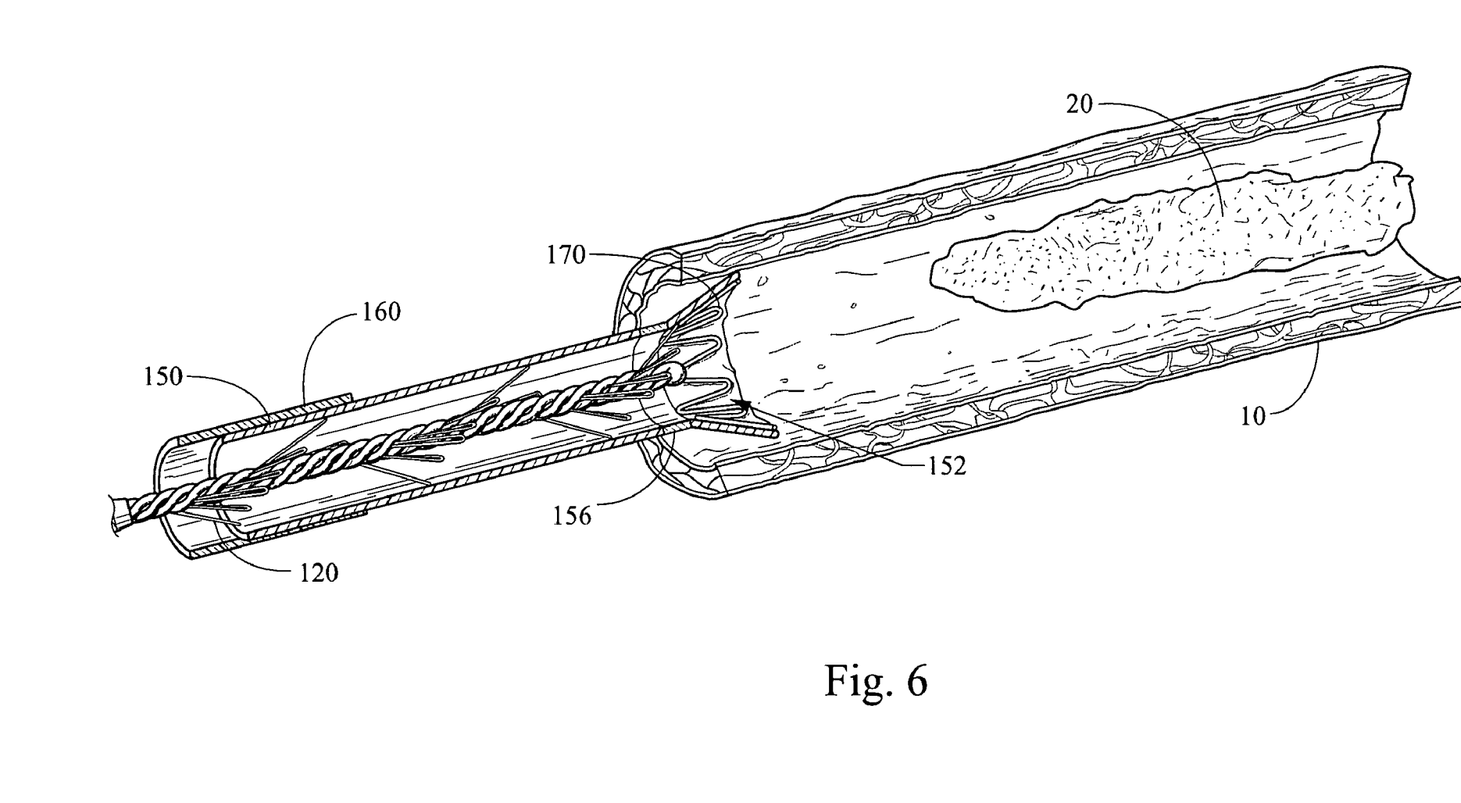
FIG. 6 is a cross-sectional view of the distal end of the thrombectomy device of FIG. 4 in an initial deployment position.
Figure 7:
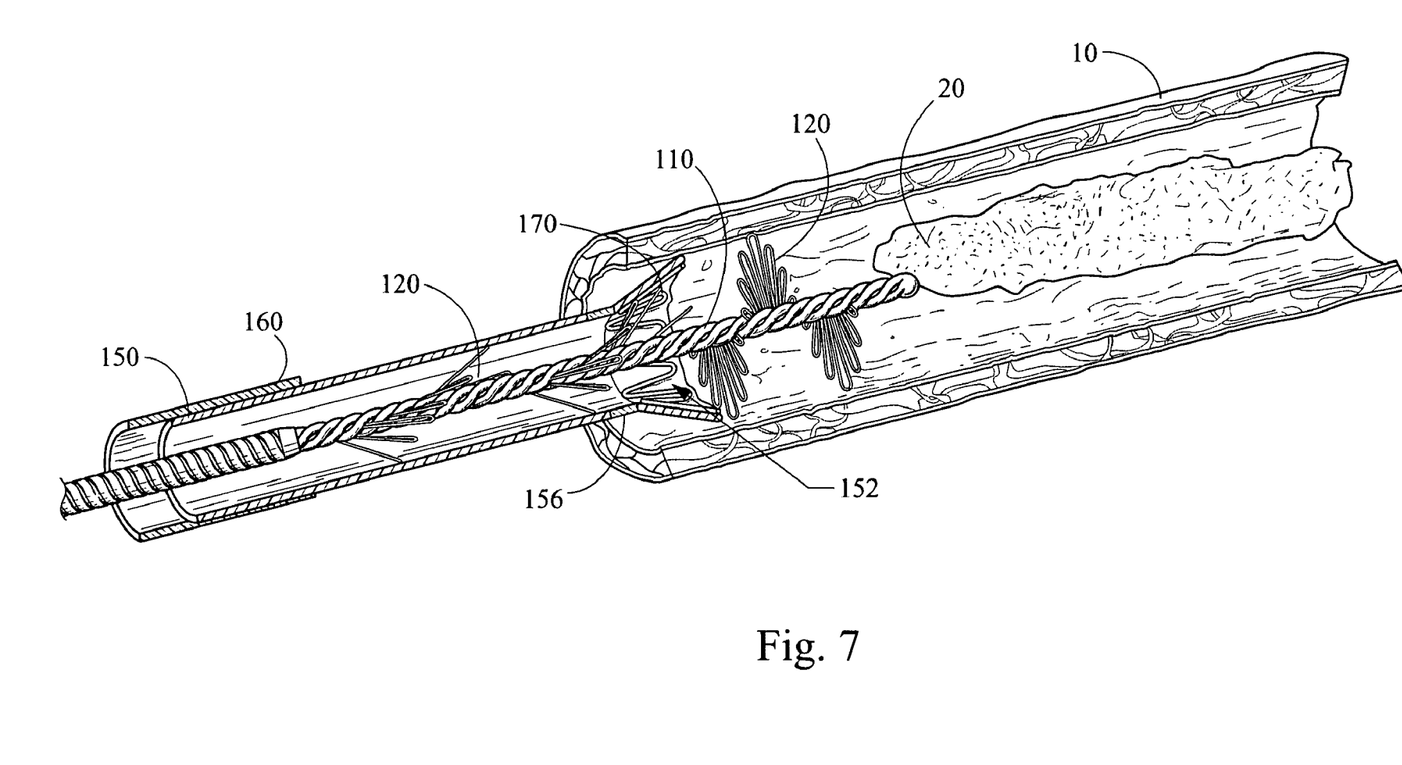
FIG. 7 is a cross-sectional view of the distal end of the thrombectomy device of FIG. 6 in an intermediate deployment position.
Figure 8:
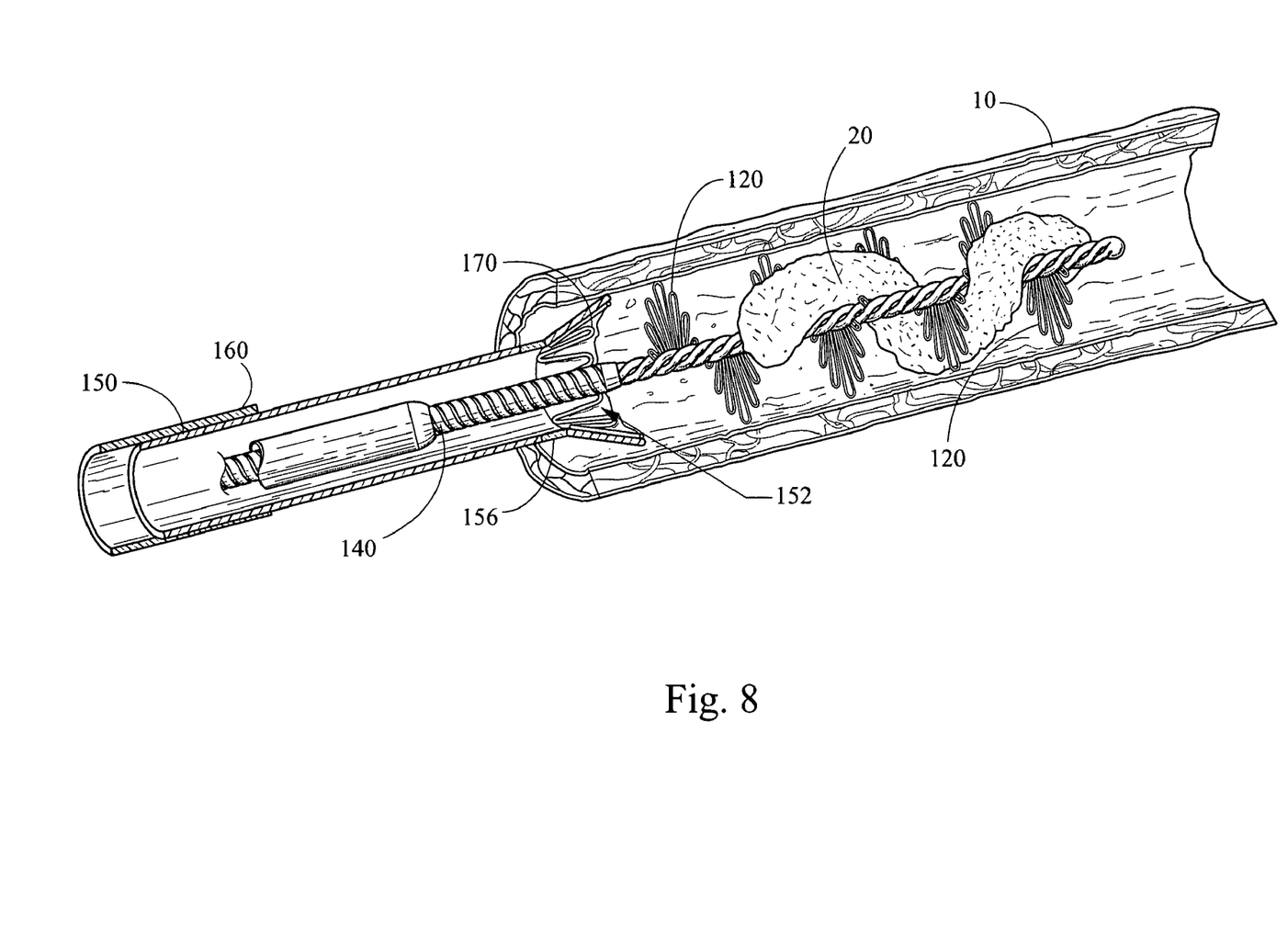
FIG. 8 is a cross-sectional view of the distal end of the thrombectomy device of FIG. 7 in a fully deployed position.

FIGS. 6-8 illustrate the operation of the delivery system 200. Initially, the delivery system 200 is inserted percutaneously and advanced into a patient's vasculature to a desired treatment site using the Seldinger technique, which is well known in the art. Initially, a guide wire may be used to insert a guide sheath to the treatment site. The guide wire may then be removed, and the delivery system 200 may be advanced to the treatment site through the guide sheath. As described above, radiopaque material doped engagement members 120, or alternatively, radiopaque markers placed on the sheaths 150, 160, may allow the thrombectomy device 100 to be visually placed at the treatment site by the physician using fluoroscopy. Preferably, the delivery system 200 is placed proximal of the thrombus 20 in the vessel or cavity.

Once the delivery system 200 has been advanced to the treatment site, the outer retention sheath 160 is withdrawn proximally by pulling the handle 191 toward the knob 196. As the outer retention sheath 160 is removed from the expandable distal portion 152, the spring member 170 is released and automatically and immediately expands out to the diameter of the vessel/cavity such that it contacts the vessel/cavity wall 10, this causes the expandable distal portion 152 to expand a corresponding amount, as shown in FIG. 6. Preferably, the thrombectomy device 100 includes a sufficient number of engagement members 120 to maintain good traction on the thrombus 120 without fragmenting the thrombus 120 or displacing it further downstream.

Next, the thrombectomy device 100 is advanced out of the inner sheath 150 using the pin vise 180. The initial advancement through the inner sheath 150 may be accomplished through linear or rotational translation by pushing or rotating the pin vise 180, respectively. As the pin vise is rotated, it turns the torque shaft 140, which turns the elongate torsion member 110 and the engagement members 120.

As the thrombectomy device 100 is advanced, the engagement members 180 automatically begin to flex in a radially outward direction as they pass through the expandable distal portion 152, and assume the fully expanded configuration such that the engagement members 150 contact the vessel/cavity wall 10. Once the engagement members 150 have contacted the vessel/cavity wall 10, the thrombectomy device 100 is preferably rotatably advanced along the vessel/cavity wall 10. Because the portions of the engagement members 120 that come in contact with the vessel/cavity wall 10 are atraumatic and present a smooth curve, the engagement members 120 can be safely expanded against the vessel/cavity wall 10 and rotatably or slidably advanced therealong without causing damage to the vessel/cavity wall 10. Moreover, by expanding the engagement members 120 against the vessel/cavity wall 10, gaps between the thrombectomy device and the vessel/cavity wall 10 are eliminated and any portions of the thrombus 20 that may break off during thrombectomy are more likely to be captured in the helical arrangement of engagement members 120.

When the distal end of the thrombectomy device 100 contacts the thrombus 20, initially, the blunt end 112 of the elongate torsion member 110 engages and forces at least a portion of the thrombus 20 to contact the distal most engagement members 120, as shown in FIG. 7.

As the thrombectomy device continues to be rotatably advanced, the thrombectomy device 100 is "screwed" into the thrombus 20, thereby causing the thrombus 120 to engage the engagement members 120. In turn, the engagement members 120 guide the thrombus 20 through the helical path defined by the engagement members 120 along the elongate torsion member 110 toward the inner sheath 150. Once the thrombus 20 is completely captured by the engagement members 120, the thrombectomy device 100 can be either rotatably or linearly withdrawn back into the inner sheath 150. As the thrombectomy device 110 is withdrawn into the inner sheath 150, the funnel shape of the expandable distal portion 152 helps collect any portions of the thrombus 20 that may have been dislodged by the engagement and retraction process, thereby preventing such particles from being released into the bloodstream. Further, the sloped inner surface of the expandable distal portion 152 helps the engagement members 120 to gradually and securely flex back to their compressed form within the inner sheath 150. After the thrombectomy device 100 and the thrombus 20 have been completely withdrawn into the inner sheath 150, the outer retention sheath 160 may be advanced forward, thereby collapsing the spring member 170. The physician may then attach a syringe or other such device to one or both of the luer locks 197 to inject or withdraw fluid as needed. The entire delivery system, including the thrombus 20, may then be withdrawn and removed from the patient.

Alternatively, the delivery system 200 may be partially inserted into the thrombus 20 with the thrombectomy device 100 still restrained in the compressed state. Once the distal end of the retention sheath 162 has been implanted into the thrombus 20, the thrombectomy device 100 is deployed and then rotatably advanced in the distal direction in a non-piercing manner to capture the thrombus 20. In this case, the rotation of the thrombectomy device 100 can be used to urge the thrombus 20 toward the collecting sheath.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A medical device for removing a thrombus, the device comprising:
    an elongate torsion member having a proximal end and a distal end; and
    a plurality of helically arranged engagement members disposed at a distal portion of said elongate torsion member, said engagement members having a collapsed state within a sheath for delivery to a treatment site within a patient wherein said engagement members are compressed toward said elongate torsion member, and an expanded state wherein said engagement members are expanded radially outward, said helically arranged engagement members being configured to twistingly engage a thrombus and guide said thrombus along a helical path defined by said plurality of helically arranged engagement members;
    wherein said engagement members are attached to and extend radially outward from said elongate torsion member at different longitudinal points along said elongate torsion member such that adjacent engagement members are spaced longitudinally and circumferentially from each other when in said expanded state, and wherein, in said expanded state at least a radially outermost portion of each of said engagement members has a rounded atraumatic shape that arcs between two sides of a loop.

2. The medical device of claim 1, wherein when deployed in a body lumen or cavity, said engagement members expand out such that said rounded atraumatic shape of said engagement members contacts a wall of said body lumen or cavity.

3. The medical device of claim 1, wherein an entirety of each of said engagement members consists of loop of wire that extends from said longitudinal point on said torsion member in a continuous manner, said loop of wire being made of a material having super-elastic characteristics.

4. The medical device of claim 3, wherein said elongate torsion member is a metallic shaft made from a flexible metallic material and said wire of each of said engagement members is permanently attached to said different longitudinal points.

5. The medical device of claim 3, wherein said elongate torsion member is a torque cable that is woven from a plurality of metallic wire strands, and wherein said wire forming said engagement members is a single continuous wire woven into said torque cable.

6. The medical device of claim 5, wherein said wire strands and said wire forming said engagement members are made of nitinol.

7. The medical device of claim 5, further comprising a torque shaft fixedly attached to said proximal end of said elongate torsion member.

8. The medical device of claim 7, further comprising a handle that engages said torque shaft such that when said handle is rotated said engagement members are also rotated.

9. The medical device of claim 1, wherein a distal tip of said torsion member has a blunt atraumatic shape.

10. The medical device of claim 7, wherein said sheath comprises a spring member disposed at a distal end thereof, said spring member having a compressed configuration in which said spring member has a diameter substantially equal to a diameter of said sheath, and an expanded configuration in which at least a portion of said spring member has a diameter that is larger than said diameter of said sheath.

11. The medical device of claim 10, wherein said spring member has a proximal end that is restrained and a distal end that is unrestrained in said expanded state, such that said spring member has a cone like shape when expanded.

12. The medical device of claim 11, wherein a distal end of said sheath comprises pleats that are folded when said spring member is in said compressed configuration, and that are unfolded when said spring member is in said expanded configuration.

13. The medical device of claim 11, wherein at least a distal portion of said sheath is made of an elastic polymer that is coupled to said spring member such that said elastic polymer stretches when said spring member moves from said compressed to said expanded configuration.

14. The medical device of claim 13, further comprising a substantially inelastic outer sheath disposed on an outer surface of said sheath and slidably movable thereupon, said outer sheath restraining said spring member in said compressed configuration.

15. A medical device for removing a thrombus, the device comprising:
1) a torque cable that is woven from a plurality of metallic wire strands, said torque cable having a proximal end and a distal end, said distal end having a blunt atraumatic shape;
2) a plurality of helically arranged engagement members disposed at a distal portion of said torque cable, said members having a collapsed state within a sheath for delivery to a treatment site within a patient wherein said engagement members are compressed radially inward, and an expanded state wherein said engagement members are expanded radially outward, wherein in said expanded state at least a radially outermost portion of each of said engagement members has a rounded atraumatic shape that arcs between two sides of a loop, said helically arranged engagement members being configured to twistingly engage a thrombus and guide said thrombus along a helical path defined by said plurality of helically arranged engagement members,
wherein each of said engagement members is a loop of wire extending from said torsion member in a continuous manner that is woven into said torque cable such that each engagement member extends radially outward from said torque cable at a different longitudinal point along said torque cable and adjacent engagement members are spaced longitudinally and circumferentially from each other when in said expanded state; and
3) said sheath being disposed around said torque cable and having a diameter that is less than a diameter of said helical arrangement of said engagement members in said expanded state, said sheath comprising a spring member disposed at a distal end thereof, said spring member having a compressed configuration in which said spring member has a diameter substantially equal to an inner diameter of said sheath, and an expanded configuration in which at least a portion of said spring member has a diameter that is larger than said diameter of said sheath,
wherein said spring member has a proximal end that is restrained and a distal end that is unrestrained in said expanded state, such that said spring member has a cone like shape when expanded.

16. The medical device of claim 1, wherein said engagement members are formed from a continuous length of wire.

17. The medical device of claim 16, wherein said wire is made of nitinol.

* * * * *

UNITED STATES PATENT AND TRADEMARK OFFICE
CERTIFICATE OF CORRECTION

PATENT NO. : 8,361,095 B2  
APPLICATION NO. : 12/372352  
DATED : January 29, 2013  
INVENTOR(S) : Thomas A. Osborne Page 1 of 1

It is certified that error appears in the above-identified patent and that said Letters Patent is hereby corrected as shown below:

In the Claims

In column 10, claim 3, line 30, after "engagement members consists of" insert --a--.

Signed and Sealed this  
Thirtieth Day of July, 2013

Teresa Stanek Rea  
*Acting Director of the United States Patent and Trademark Office*